US009868026B2

(12) United States Patent
Marcandelli et al.

(10) Patent No.: US 9,868,026 B2
(45) Date of Patent: Jan. 16, 2018

(54) FUNCTIONAL POSTURAL TRAINING MACHINE (71) Applicant: TECNOBODY S.R.L., Dalmine (BG) (IT)

(72) Inventors: Stefano Marcandelli, Stezzano (IT); Alessandro Carminati, Stezzano (IT)

(73) Assignee: TECNOBODY S.R.L., Dalmine (BG) (IT)

( * ) Notice: Subject to any disclaimer, the term of this patent is extended or adjusted under 35 U.S.C. 154(b) by 0 days.

(21) Appl. No.: 15/116,721

(22) PCT Filed: Feb. 2, 2015

(86) PCT No.: PCT/IB2015/050783
§ 371 (c)(1),
(2) Date: Aug. 4, 2016

(87) PCT Pub. No.: WO2015/118439
PCT Pub. Date: Aug. 13, 2015

(65) Prior Publication Data
US 2016/0346601 A1 Dec. 1, 2016

(30) Foreign Application Priority Data
Feb. 5, 2014 (IT) .............................. BG2014A0003

(51) Int. Cl.
*A63B 24/00* (2006.01)
*A63B 23/035* (2006.01)
(Continued)

(52) U.S. Cl.
CPC ...... *A63B 23/03541* (2013.01); *A61B 5/1036* (2013.01); *A61B 5/11* (2013.01);
(Continued)

(58) Field of Classification Search
CPC . A63B 24/00; A63B 24/0062; A63B 24/0087; A63B 24/0075; A63B 23/08;
(Continued)

(56) References Cited

U.S. PATENT DOCUMENTS 4,912,638 A * 3/1990 Pratt, Jr. .............. A61B 5/1121
128/905
5,540,642 A 7/1996 Sprague
(Continued)

FOREIGN PATENT DOCUMENTS

WO 2012128612 A1 9/2012

*Primary Examiner* — Glenn Richman
(74) *Attorney, Agent, or Firm* — King & Schickli, PLLC (57) ABSTRACT

Machine for functional postural training of a user (13) comprising: a platform (12) comprising a plurality of load cells (20) on which said user (13) is positioned; extendable cables (15, 42) provided with handle (16, 43); means (50) for providing said cables (15, 42) with a certain load; means (23) for detecting the dynamic posture of said user (13) during the exercise; means (23, 49) for determining the various body segments of said user on the basis of the information received from said means (23) for detecting the dynamic posture of said user (13); means (49) for calculating the center of pressure of said user (13) on the basis of the information provided by said plurality of load cells (20); means (22) for displaying the center of pressure of the user (13) on said platform (12) and means (22) for displaying said body segments of said user (13); means (49) for comparing said body segments of said user (13) with corresponding body segments stored in memory; means (22) for warning said user (13) if there are differences between said body segments of said user (13) and said body segments stored in memory; means (22) for warning said user (13) that the position of said center of pressure has changed.

8 Claims, 7 Drawing Sheets (51) Int. Cl.
| | |
|---|---|
| *A63B 71/06* | (2006.01) |
| *A61B 5/103* | (2006.01) |
| *A61B 5/11* | (2006.01) |
| *A63B 21/008* | (2006.01) |
| *A63B 23/02* | (2006.01) |
| *A63B 23/12* | (2006.01) |
| *A63B 21/00* | (2006.01) |
| *A63B 21/055* | (2006.01) |
| *A63B 71/00* | (2006.01) |

(52) U.S. Cl.
CPC .......... *A61B 5/1116* (2013.01); *A61B 5/1121* (2013.01); *A63B 21/0087* (2013.01); *A63B 21/0552* (2013.01); *A63B 21/154* (2013.01); *A63B 21/4035* (2015.10); *A63B 21/4043* (2015.10); *A63B 23/0244* (2013.01); *A63B 23/1209* (2013.01); *A63B 24/0087* (2013.01); *A63B 71/0622* (2013.01); *A63B 2071/0072* (2013.01); *A63B 2071/068* (2013.01); *A63B 2071/0627* (2013.01); *A63B 2071/0636* (2013.01); *A63B 2071/0652* (2013.01); *A63B 2220/16* (2013.01); *A63B 2220/52* (2013.01); *A63B 2220/806* (2013.01); *A63B 2220/836* (2013.01); *A63B 2220/89* (2013.01)

(58) Field of Classification Search
CPC . A63B 69/36; A63B 21/0083; A63B 21/4049; A63B 22/0292; A63B 23/03541; A63B 23/0244; A63B 23/1209; A63B 71/0622; A63B 21/0087; A63B 21/4043; A63B 21/4035; A63B 21/0552; A63B 21/154; A63B 2071/0636; A63B 2071/068; A63B 2071/0652; A63B 2071/0627; A63B 2071/0072; A63B 2220/836; A63B 2220/89; A63B 2220/806; A63B 2220/52; A63B 2220/16; A61B 5/1036; A61B 5/11; A61B 5/1121

See application file for complete search history.

(56) References Cited

U.S. PATENT DOCUMENTS

| | | | |
|---|---|---|---|
| 8,100,770 B2 | 1/2012 | Yamazaki et al. | |
| 9,446,288 B1* | 9/2016 | Pazan | A63B 24/0087 |
| 2004/0043873 A1 | 3/2004 | Wilkinson et al. | |
| 2004/0204294 A2 | 10/2004 | Wilkinson et al. | |
| 2005/0148432 A1 | 7/2005 | Carmein | |
| 2007/0037663 A1* | 2/2007 | Goel | A63B 69/36 482/1 |
| 2007/0232450 A1* | 10/2007 | Hanoun | A63B 21/0083 482/1 |
| 2008/0261696 A1 | 10/2008 | Yamazaki et al. | |
| 2012/0015777 A1* | 1/2012 | Goel | A63B 21/4049 482/4 |
| 2012/0108392 A1* | 5/2012 | Chu | A63B 22/0292 482/4 |
| 2015/0306459 A1* | 10/2015 | Boyette | A63B 24/0075 482/5 |
| 2015/0328497 A1* | 11/2015 | Doucot | A63B 23/08 482/146 |

* cited by examiner

FUNCTIONAL POSTURAL TRAINING MACHINE

The present invention refers to a functional postural training machine.

As is known, two main types of machine are used in fitness gyms: machines for cardiovascular training and machines for building muscle strength, known more simply as cardio circuit and isotonic circuit.

In the 80s and up to the beginning of the 2000s only the traditional isotonic machines existed, based on the concept that each machine develops in a precise manner the muscular strength and power of a specific muscle area.

In this context, many firms in the past, and still today, have developed a complete range of 15-20 machines with the aim of covering as comprehensively as possible all the muscle areas of the human body.

In the last 10 years a different concept, that of Functional Training, has become increasingly widespread for developing strength.

The principle is logical and very simple. Ordinary people, as well as professional athletes, need to train not only the individual muscle but the function.

An example better illustrates this concept: when we lift a bag of shopping, we do not use just one single muscle area: we naturally activate a muscle chain to perform the function required. In technical terms, this activation is called motor patterns.

As previously mentioned, this new approach has revolutionised the gym world, switching from a very specific muscle training to a more complex and global training.

This new training approach has attracted a new very different user group to the gym, more attentive to general physical condition than to appearance.

The machines which, over the last ten years, have brought about this conceptual shift are Functional Trainer systems based essentially on cables.

In short, these systems are simply an evolution of the classic Ercolina with cables adapted to respond better to certain strengthening exercises.

One of the fundamental characteristics of Functional Trainer machines, in order for them to be correctly defined as such, is that they must allow exercise in a standing position, since human beings lift loads and make the greatest physical effort not in a sitting position but in a standing position.

It is no accident that the majority of traumas and general injuries occur when carrying out movements in a standing position, when the person is off-balance and incorrectly manages the levers of his/her body.

The object of the present invention is to provide an improved functional training machine with respect to those of the known art.

A further object is to provide a machine able to give the user immediate information on his/her posture during a weight-bearing isotonic exercise under stress such as a Functional Trainer exercise.

According to the present invention, said objects and others are achieved by a functional postural training machine comprising: a platform including a plurality of load cells on which the person is positioned; extendable cables provided with handle; means for providing said cables with a certain load; means for detecting the dynamic posture of said person during the exercise; means for determining the various body segments of said person on the basis of the information received from said means for detection of the dynamic posture of said person; means for calculating the centre of pressure of said person on the basis of the information provided by said plurality of load cells; means for displaying the centre of pressure of the person on said platform and means for displaying said body segments of said person; means for comparing said body segments of said person with corresponding body segments stored in memory; means for warning said person if there are differences between said body segments of said person and said body segments stored in memory; means for warning said person that the position of said centre of pressure has changed.

Said objects are furthermore achieved by a functional training method comprising the steps of providing a person with a pair of extendable cables to which a predetermined load is applied; determining the centre of pressure of said person positioned on a platform provided with a plurality of load cells; detecting the dynamic posture of said person by means of a three-dimensional detection system; determining the various body segments of said person; warning said person that the position of said centre of pressure has changed; warning said person that his/her posture, defined by said body segments, is not correct.

Further characteristics of the invention are described in the dependent claims.

This solution has various advantages with respect to the solutions of the known art.

The present invention proposes a classic Functional Trainer cable system having at the base a platform with stabilometric load cells for detecting the centre of pressure during exercise.

When the person has to sustain a certain load equally distributed with the cables on the RH and LH hemisoma, the present invention shows how said person manages his/her centre of pressure on the ground (COP) under a load.

If one part of the body, e.g. RH hemisoma, is weaker than the contralateral part, the person will inevitably shift his/her centre of pressure to the weak part of the body with evident load distribution problems if not adequately corrected.

The present invention also comprises an integrated system for detecting the dynamic posture during exercise.

Said system can be produced with inertial sensors applicable on the body of the user, so as to obtain a very precise system.

Otherwise the system can be produced by using a 3D (three-dimensional) camera applied frontally on the user.

The objective of the camera is identical to that of the inertial sensors, i.e. to give the user, via a screen, a series of indications on his/her posture during the functional exercise.

The innovative aspect lies in the combination of these three worlds which up to now have been considered separately, i.e. the postural-proprioceptive world, the world of classic functional trainer devices, and the world of movement analysis.

The user can strengthen the weakest part of his/her muscle chain by observing how his/her posture changes during a muscle exercise.

Furthermore, due to the 3D camera or inertial sensors, the system allows real-rime monitoring not only of the centre of pressure of the person on the load platform but also the entire posture of the various body segments.

Control of the trunk is of fundamental importance. A person's postural stability depends largely on control of the trunk including the upper, lower and pelvic areas. This anatomical part is the pivot of our body. If not correctly managed and "felt" by our nervous system, postural problems will inevitably arise.

The classic example that illustrates the importance of control of the trunk is to teach a person that when he/she lifts a weight from the ground, he/she must adopt a slightly lordotic stance and raise the load not with the back but with the legs.

The system allows normal movements to be performed under stress with real-time control of the posture and correction of the latter when wrong.

With this system, the person immediately perceives the meaning of posture and how it can vary during a daily life exercise under stress.

Virtual reality interface software is particularly useful and innovative.

This software reproduces on the computer screen movements performed in everyday life, for example lifting two bags of shopping with both arms.

The software shows at the side of the screen how the person's centre of pressure changes on the ground and the inertial sensors or the 3D camera highlight the new postural position of the person when subject to a load.

The load to which the user is subject, which varies according to the situation due to a pneumatic system electronically controlled by the computer, is particularly important.

In this way the load to which the person is subject is always variable in relation to different surroundings or tasks to be carried out in the virtual environment (lifting bottles, holding a crate with both hands, raising a roll-up shutter, lowering a roll-up shutter, moving a bag from right to left, etc.).

The characteristics and advantages of the present invention will become evident from the following detailed description of a practical embodiment thereof, illustrated by way of non-limiting example in the accompanying drawings, in which.

Figure 1:
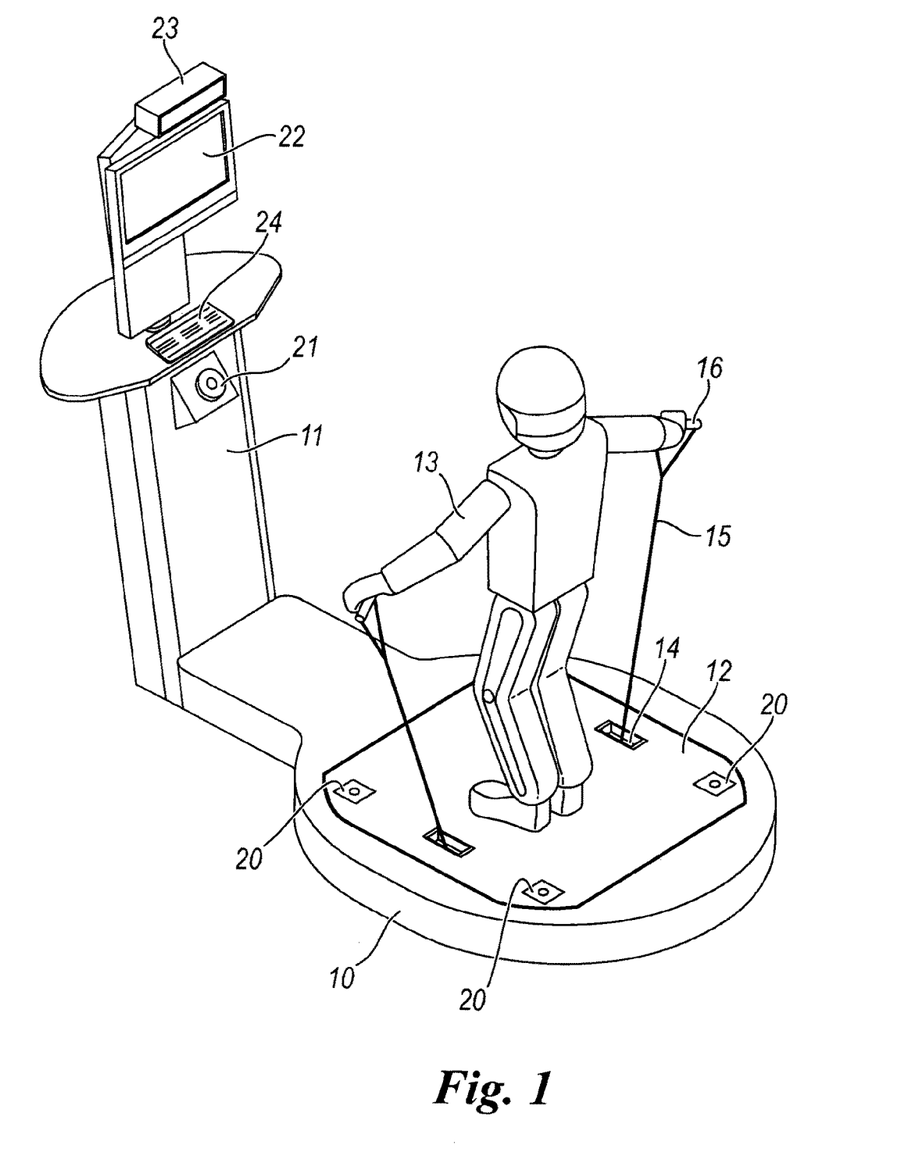
FIG. 1 shows schematically a functional training machine according to a first embodiment of the present invention.

Referring to the attached figures, a functional training system, according to a first embodiment of the present invention, comprises a base 10. A vertical frontal structure 11 rises from the base 10.

The base 10 is provided with a stabilometric platform 12, having dimensions for example of 100×100 cm, on which a user stands.

On the base 10 and laterally to the platform 12 are two slots 14 from which two cables 15 protrude terminating in two handles 16, which are gripped by the user 13.

The cables 15, inside the machine, are connected by pulleys to a pneumatic piston which is adjustable, preferably automatically, appropriately arranged inside the machine.

The stabilometric platform 12 comprises four load cells 20 arranged preferably in the vicinity of the four corners of the same, or in any case arranged in the vicinity of the edges of the platform 12.

The sensors 20 allow determination of each single force applied to the platform 12 and its intensity (Kg) and the position of the centre of pressure are determined. The centre of pressure is assessed considering the measurements taken by each single sensor 20.

In particular, the centre of mass of the system formed of the four forces that strike the sensors 20 is calculated.

Figure 7:
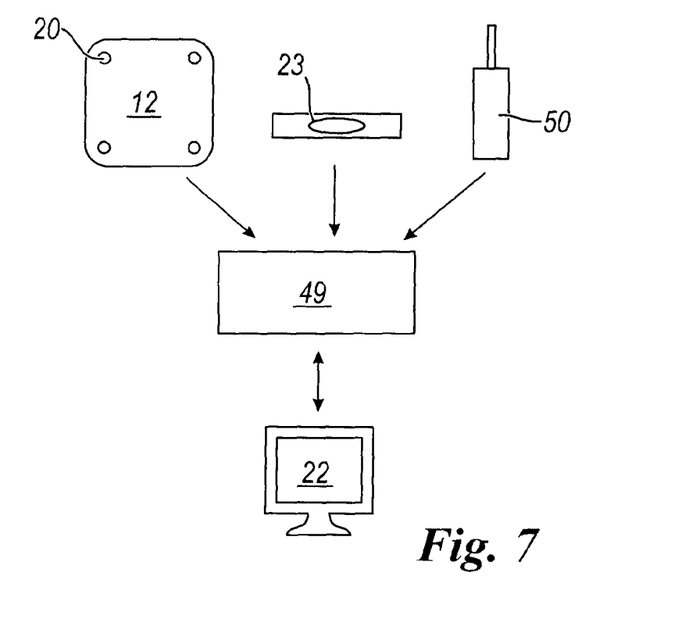
FIG. 7 shows schematically a control and management system of a functional training machine according to the present invention.

All the sensors 20 are connected to a control centre 49 in asynchronous mode with frequency that can be configured from 20 Hz to 40 Hz.

Alternatively to the sensors 20 it is possible to use an array of piezoresistive sensors, for example baropodometric platforms.

On the frontal vertical structure 11, it is possible to provide a manual control 21 for adjustment of the loads applied to the handles. Alternatively, said control may be absent as the entire system is programmed automatically.

Always on the vertical structure 11, a control panel 22 for the system, preferably a touch screen, is provided at eye level. It, allows the viewing of information but it can also receive input commands. A keyboard 24 can also be used, alternatively or in combination.

Near the control panel 22 there is also a 3D detection system 23 for detecting the posture of the user.

The Microsoft Kinect® system has been used, for example, as the 3D detection system 23.

The above system consists of a video camera and dual infrared depth sensor, composed of an infrared laser scanner and a camera sensitive to the infrared rays of the laser. Kinect® is also provided with microphones able to reduce the background noise and correctly recognise voice commands.

The system 23 used for detecting the movements is able to detect articular movements in angle degrees with a precision varying from 2° to 5° on the three movement planes.

The system 23 by means of the 3D vision identifies the movements of the person which can be seen on the control panel 22.

The system 23 identifies the various body segments (for example, arms, legs, pelvis, trunk, if necessary further divided at the joints) and shows them schematically on the control panel 22. The control centre 49 has stored in memory the correct position for the exercise performed and is therefore able to provide the user with information concerning the correct or incorrect posture, comparing the positioning of the body segments identified with those in memory. The comparison is made by comparing each body segment acquired with the respective body segment stored in memory and indicating the variations, for example variations in inclination of said segments.

In particular it is able to clearly indicate (by sound and/or light indication on the control panel 22) whether the postures compared show variations so that the user can correct them.

Alternatively to the Kinect system, it is possible to use a series of inertial sensors positioned on the user's body, arranged at appropriate points and connected to the machine control system.

Figure 2:
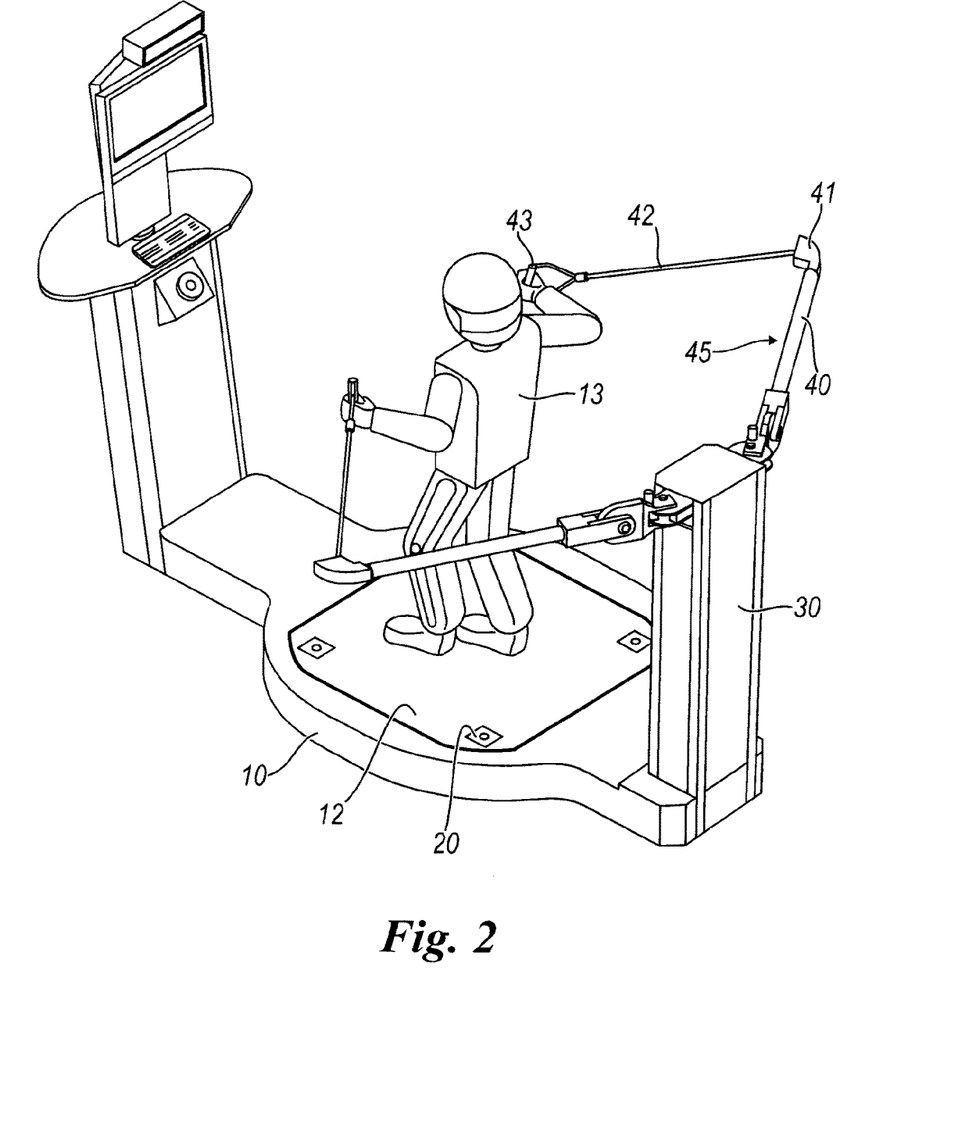
FIG. 2 shows schematically a functional training machine according to a second embodiment of the present invention.

In a second embodiment of the present invention, the system comprises a vertical structure 30 at the rear of and opposite to the structure 11, which rises from the base 10. In this case, the slots 14 are not present.

Figure 3:
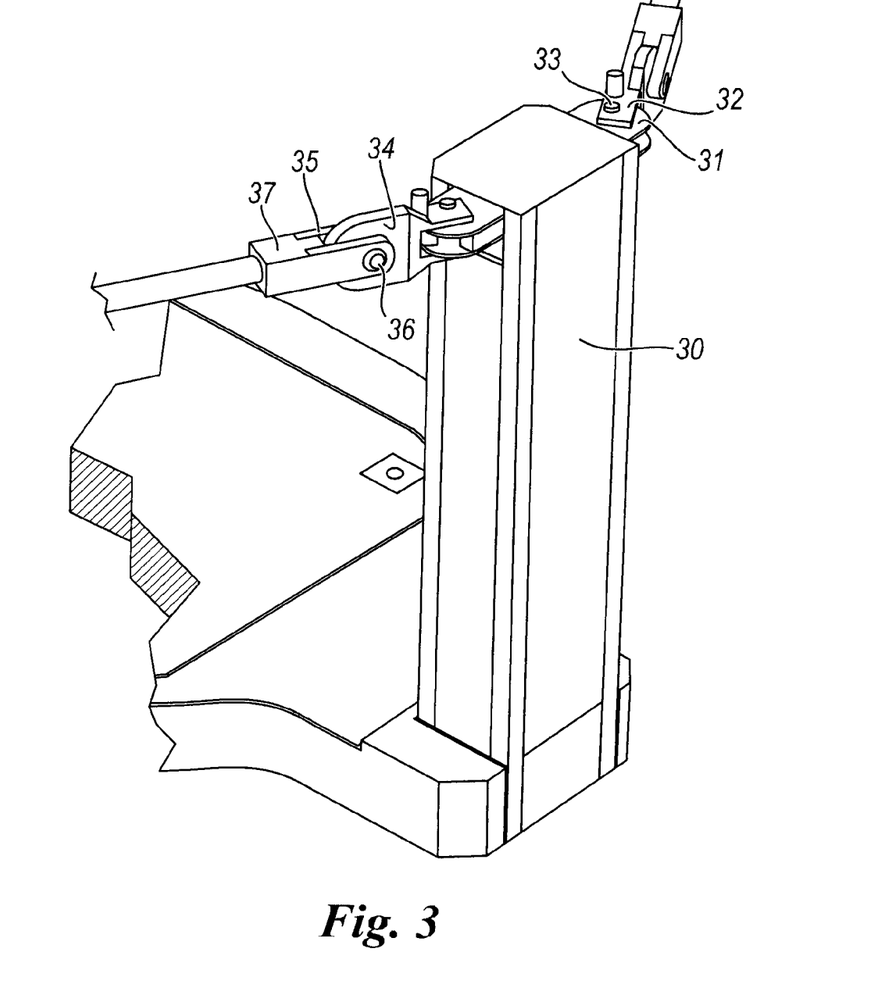
FIG. 3 shows schematically a detail of the functional training machine according to a second embodiment of the present invention.

The structure 30 reaches the height of the back/shoulders of the user. At the top, two horizontal plates 31 project laterally. Each of said plates is connected to a first fork 32 revolving around a vertical pin 33, which fixes it to the plate 31.

Each of the forks 32 continues with a vertical plate 34. The fork 32 and the plate 34 are formed in one single piece.

To each plate 34, a second fork 35 is fixed revolving around a horizontal pin 36, which fixes it to the plate 34.

Each of the forks 35 continues with a bar 37.

The fork 35 and the bar 37 are formed in one single piece.

To the bar 37 a tubular element 40 is fixed, approximately 130 cm long, which terminates in a pulley 41.

A cable 42 terminating in a handle 43 comes out of each pulley 41.

The cable 42 passes inside the tubular element 40, the bar 37, the plate 34, the plate 31, and enters the structure 30.

The tubular element 40, the bar 37, the plate 34 and the plate 31 are appropriately drilled so that the cable 42 can pass through.

The cable 42 inside the structure 30 is carried by appropriate pulleys until it reaches the adjustable pneumatic piston.

The structure described above forms two arms 45 symmetrical to each other.

Figure 4:
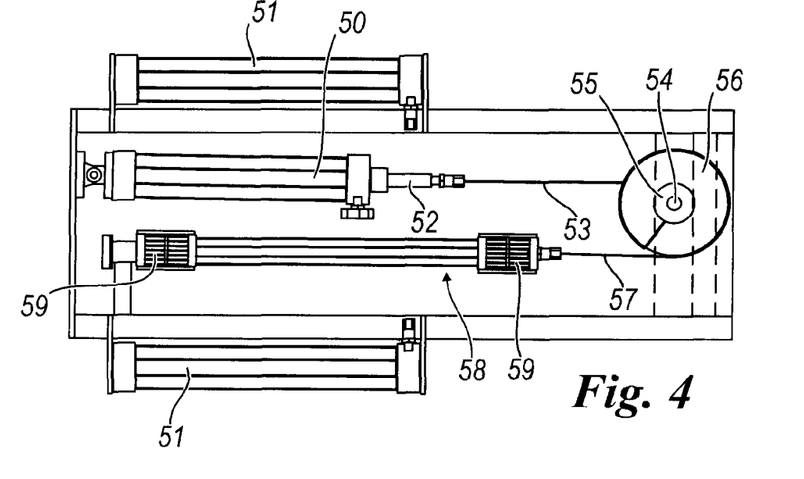
FIG. 4 shows schematically a pneumatic actuator of a functional training machine according to the present invention.

The pneumatic actuator which opposes resistance to the cables 42 or 15 uses an adjustable pneumatic piston 50. The piston 50 is connected by means of a tube (not shown) to two air reservoirs 51.

Figure 6:
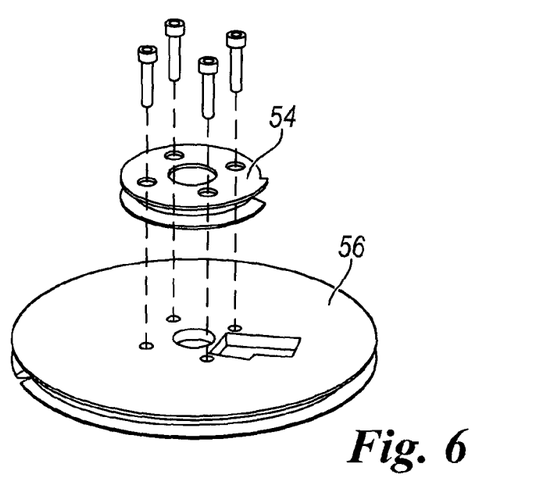
FIG. 6 shows schematically a pair of pulleys used in a pneumatic actuator of a functional training machine according to the present invention.

The stem 52 of the piston 50 is connected to a cable 53 which reaches a pulley 54 with variable radius, i.e. it has a tapered axis.

The pulley 54 rotates around an axis 55 and is fixed to another pulley 56, with constant radius, with larger dimensions than the pulley 54, also rotating around the axis 55.

Figure 5A:
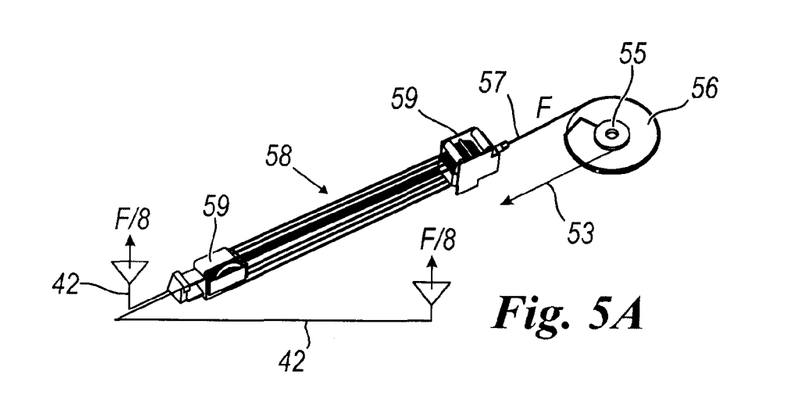
FIGS. 5a and 5b show schematically a detail of the pneumatic actuator with the cables retracted and extracted respectively of a functional training machine according to the present invention.
Figure 5B:
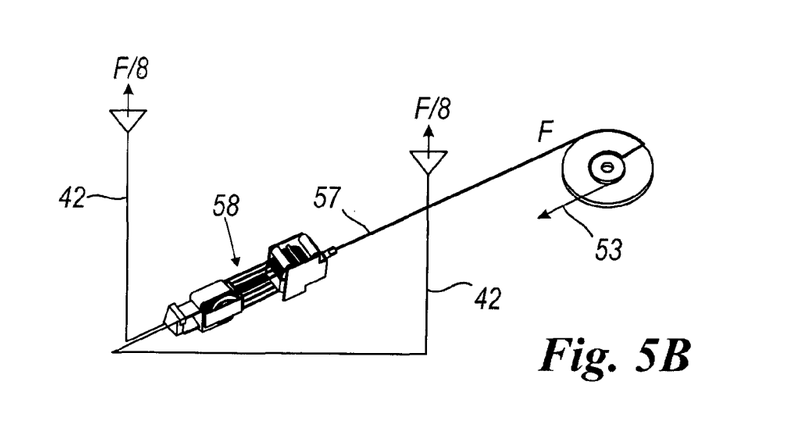

The pulley 54 is fastened to a cable 57 which connects to a pulley tackle 58 with four pulleys 59 on each side. Around these eight pulleys 59 one single cord is wound, at the end of which two handles are fastened. In practice the cords coming out of the pulley tackle 58 are cords 15 and 42. The force applied to the handles 16 and 43 is ⅛ of the force applied to the pulley tackle 58 by the cable 57.

The resistance applied to the handles is generated by compression of the volume of air inside the piston 50.

By modifying the pressure exerted on the surface of the piston, the mechanical resistance applied to the handles can be modified. The pressure can be modified, for example, via the manual control 21 or automatically by means of a control system 49 which acts on an appropriate valve.

During the movement of the piston, the volume of air inside the piston is reduced causing an increase in the internal pressure. This means that the resistance opposed to the movement of the piston is not constant during its travel.

To minimise this effect, the total volume of the air of the piston 50 is increased, adding the reservoirs 51 connected to the piston 50. In this way the variation in volume due to the movement of the piston becomes a small part of the total volume, therefore the consequent increase in pressure is significantly reduced. To make the workload constant during the entire movement, the resistance is further corrected by inserting a variable arm lever which is provided by means of the pulley 54 with variable radius. In particular, the pressure increase is balanced by the continuous reduction in the radius of the pulley 54.

In this way a pneumatic system is obtained able to maintain the workload constant.

The sensors 20, 3D detection system 23 and pneumatic piston 50 communicate with a control system 49, which is connected to the control panel 22 which displays the operations and receives in input commands via the touch screen.

The control system 49 processes the data received from the sensors 20, calculates the centre of pressure and sends information to the control panel 22 which displays the position of the centre of pressure.

In particular it is able to clearly indicate (by sound and/or light indication on the control panel 22) whether the centre of pressure varies its position with respect to its central position, so that the user can correct his/her posture. It also receives the information from the 3D detection system 23 and monitors all the user movements.

The system 23 identifies the user's movements, and in particular the various body segments, which can be seen on the control panel 22. Said movements are also monitored by the control system 49 which informs the user, via the control panel 22, of any incorrect postures, comparing them with those stored in memory. It also informs the user if the centre of pressure is maintained in the correct position or if it is altered.

The machine is designed to perform three main functions: firstly evaluation, secondly training and thirdly time programming of the training. In all cases, the monitoring allows real-time display of all the physical variables at play during the assessment and training.

The system also allows guided training to be performed.

Each training and/or assessment is performed via a guided procedure which helps the user, once he/she is standing on the platform, to use the system independently. The user selects the muscle area he/she wishes to work on and the machine indicates on what and how to perform the exercise. The exercise is performed with visual feedback (via the 3D vision system) and automatic control of correct balance and posture.

Furthermore, if the system detects an incorrect posture, it automatically modifies the attenuator loads to prevent the user overloading an anatomical area not perfectly balanced in terms of posture.

Figure 8:
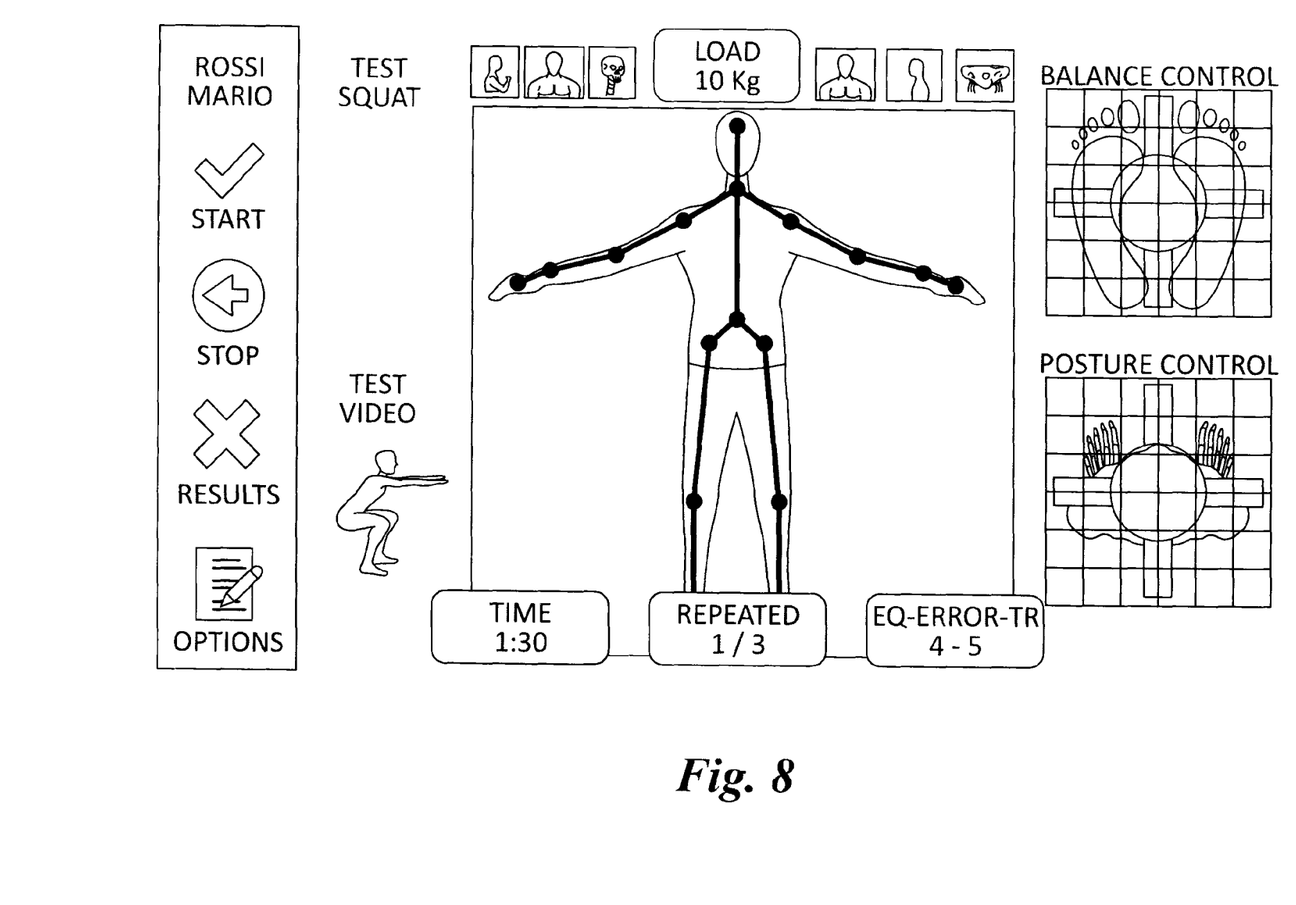
FIG. 8 shows a screen shot of the display and control system.

From a screen shot example of the control panel 22, shown in FIG. 8, on the left a column can be seen dedicated to the input of machine commands, such as start, stop, results and options. On the right are the screen shots relative to display of the information obtained from the sensors 20 of the stabilometric platform 12, i.e. the balance control (above), and the information obtained from the 3D detection system 23, i.e. control of the trunk (below). In the centre of the screen various information is provided including the position of the various body segments and then the overall posture, so that the person and his/her body segments can be seen.

Figure 9:
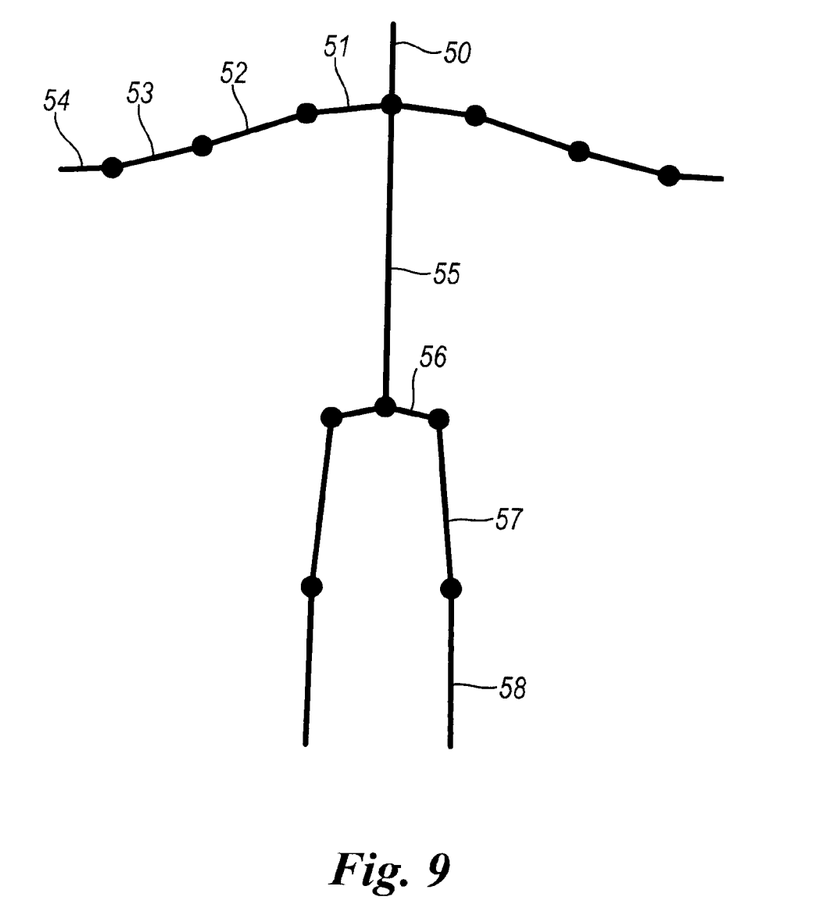
FIG. 9 shows schematically the body segments of a user, according to the present invention.

FIG. 9 shows an example of representation of the body segments of a user in the rest position. The reference number 50 shows the head, 51 the shoulder, 53 the arm, 54 the forearm, 55 the hand, 55 the trunk, 56 the hip, 57 the thigh and 58 the leg.

Any materials and dimensions can be used, according to requirements and the state of the art.

The system thus conceived is subject to numerous modifications and variations, all falling within the scope of the inventive concept; furthermore, all the details can be replaced by technically equivalent elements.

The invention claimed is:

1. Machine for the functional postural training of a person (13) comprising: a platform (12) comprising a plurality of load cells (20) on which said person (13) is positioned; extendable cables (15, 42) provided with handle (16, 43); means (50) for providing said cables (15, 42) with a given load; means (23) for detecting the dynamic posture of said person (13) during the exercise; means (23, 49) for determining the various body segments of said person on the basis of the information received from said means (23) for detecting the dynamic posture of said person (13); means (49) for calculating the centre of pressure of said person (13) on the basis of the information provided by said plurality of load cells (20); means (22) for displaying the centre of pressure of the person (13) on said platform (12) and means (22) for displaying said body segments of said person (13); means (49) for comparing said body segments of said person (13) with corresponding body segments stored in memory; means (22) for warning said person (13) if there are differences between said body segments of said person (13) and said body segments stored in memory; means (22) for warning said person (13) that the position of said centre of pressure has changed.

2. Machine according to claim 1 characterised in that said means (50) for providing said cables (15, 42) with a given load comprise a pneumatic piston (50) having a stem (52); one end of a cable (53) is connected to said stem (52), and a first pulley (54) with variable radius is connected to the other end of said cable (53); said first pulley (54) is fixed to a second pulley (56); said first (54) and second (56) pulley rotate around the same axis (55); said second pulley (56) is connected by means of a cable (57) to a pulley tackle (58); said extendable cables (15, 42) provided with handle (16, 43) protrude from said pulley tackle (58).

3. Machine according to claim 1 characterised in that said means (23) for detecting the dynamic posture comprise a three-dimensional detection system.

4. Machine according to claim 1, characterised in that said means (23) for detecting the dynamic posture comprise a three-dimensional display system which identifies the various body segments.

5. Machine according to claim 3 characterised in that said means (23) for detecting the dynamic posture comprise a plurality of inertial sensors positioned on the body of said person and connected to a control system (49) of said machine.

6. Machine according to claim 1 characterised in that said display means (22) comprise a touch screen.

7. Machine according to claim 1 characterised in that said load cells (20) are arranged in the vicinity of the edges of said platform (12).

8. Machine for the functional postural training of a person, comprising:
- a platform for receiving the person, the platform including a plurality of load cells;
- extendable cables with a handle for being gripped by the person;
- a piston for providing said cables with a given load;
- a plurality of sensors for detecting a dynamic posture of the person;
- a detector for detecting a position of body segments of the person on the basis of the information received from the plurality of sensors for detecting the dynamic posture of the person;
- a calculator for calculating the center of pressure of the person based on information from the plurality of load cells;
- a display for displaying the center of pressure of the person on said platform, and for displaying the position of the body segments of the person;
- a controller for comparing the position of the body segments of the person with a stored position, and for warning the person of differences between the position and the stored position and that the center of pressure has changed.

* * * * *